Figures 1, 2:
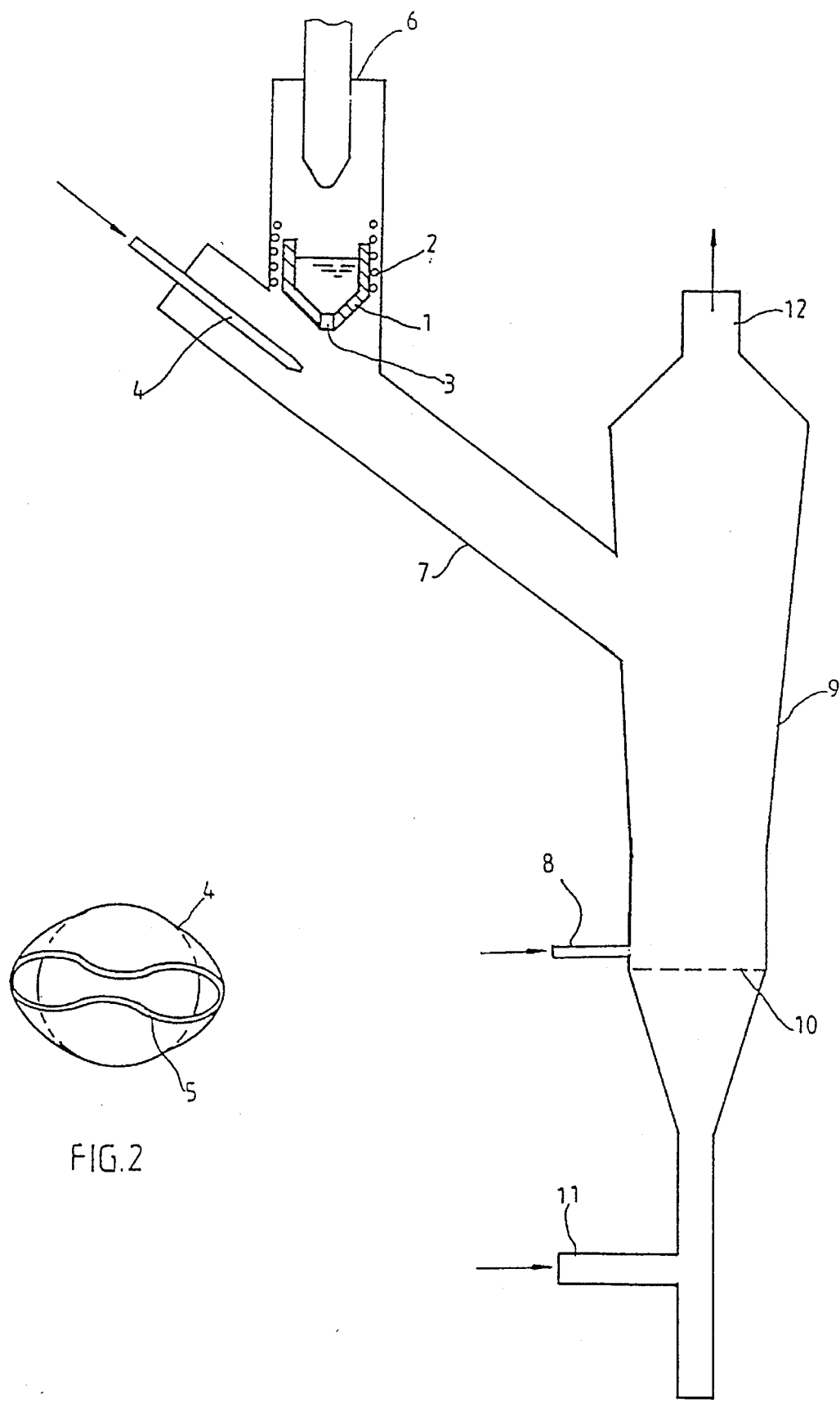

United States Patent [19]

Schulze et al.

[11] Patent Number: 5,618,960

[45] Date of Patent: Apr. 8, 1997

[54] FINE PARTICLE SILICON CONTAINING SURFACE-BOUND HALOGEN, A PROCESS FOR ITS PRODUCTION AND ITS USE

[75] Inventors: Manfred Schulze, Leichlingen; Hans Rinkes, Cologne; Elke Licht, Leverkusen; Alfred Börsting, Linz/Rhein; Bruno Degen, Much; Hans-Heinrich Moretto, Leverkusen; Gebhard Wagner, Odenthal, all of Germany

[73] Assignee: Bayer Aktiengesellschaft, Leverkusen, Germany

[21] Appl. No.: 140,108

[22] PCT Filed: Apr. 30, 1992

[86] PCT No.: PCT/EP92/00943

§ 371 Date: Oct. 27, 1993

§ 102(e) Date: Oct. 27, 1993

[87] PCT Pub. No.: WO92/19626

PCT Pub. Date: Nov. 12, 1992

[30] Foreign Application Priority Data

May 9, 1991 [DE] Germany .......................... 41 15 183.6

[51] Int. Cl.$^6$ ....................................................... C07F 7/10
[52] U.S. Cl. ........................ 556/473; 556/472; 423/348
[58] Field of Search .................................. 423/348, 341; 556/472, 473

[56] References Cited

U.S. PATENT DOCUMENTS

| 4,172,883 | 10/1979 | Ingle et al. | 423/348 |
| 4,837,376 | 6/1989 | Schwirtlich et al. | 423/348 |
| 5,118,486 | 6/1992 | Burgie et al. | 423/349 |
| 5,128,116 | 7/1992 | Forwald et al. | 423/348 |

*Primary Examiner*—Michael Lewis
*Assistant Examiner*—Stuart L. Hendrickson
*Attorney, Agent, or Firm*—Sprung Horn Kramer & Woods

[57] ABSTRACT

In the production of an organochlorosilane by reaction of silicon with at least one of an alkyl or aryl chloride in the presence of a copper catalyst, the improvement which comprises employing as the silicon fine-particle silicon containing surface-bound chlorine produced by contacting fine-particle silicon in reactive form with gaseous or liquid chlorine.

11 Claims, 1 Drawing Sheet

FINE PARTICLE SILICON CONTAINING SURFACE-BOUND HALOGEN, A PROCESS FOR ITS PRODUCTION AND ITS USE

This invention relates to fine-particle silicon containing surface-bound halogen, more particularly chlorine, to a process for its production by reaction of the silicon surface with silicon tetrahalide and to the use of the fine-particle silicon for the production of organohalosilanes in Rochow's synthesis.

Fine-particle silicon is industrially used in large quantities for the production of organochlorosilanes, more particularly methyl chlorosilanes, by direct reaction with methyl chloride in the presence of copper catalysts and, optionally, other promoters ("Rochow's synthesis", U.S. Pat. No. 2,380,905).

A number of more recent works concentrate on the specific use of trace elements, so-called promoters, in the catalyst system to make the reaction more effective, cf. for example DE-A 3 425 424, EP-A 138 678, EP-A 138 679, DE-A 3 501 085, EP-A 191 502, EP-A 194 214, EP-A 195 728, EP-A 223 447.

Other works are concerned with purity requirements and physical characteristics of silicon suitable for Rochow's synthesis, cf. for example U.S. Pat. No. 3,133,109, U.S. Pat. No. 4,500,724 and EP-A 350 683.

The present invention is based on extensive investigations into the effect which the surface of fine-particle silicon has on Rochow's synthesis. Although silicon reacts relatively sluggishly and hence undergoes hardly any changes in the atmosphere, it passes through stages of high reactivity in the production of fine particles having particle sizes of 20 to 500 μm (depending on the particular reactor system used for Rochow's synthesis). These high-reactivity stages are, for example, freshly broken surfaces where the fine-particle silicon is produced by grinding of coarse-particle silicon or the surface of silicon melt droplets or the already solidified fine-particle silicon at temperatures above about 1,000° C. where the fine-particle silicon is obtained by atomization of a silicon melt.

The reactivity of fine-particle silicon is critically affected by surface reactions with oxygen, atmospheric moisture, carbon dioxide or other constituents of the surrounding atmosphere during the reactive stage.

It has now been found that the reactivity (i.e. reaction rate and selectivity towards the formation of dimethyl dichlorosilane in the reaction with methyl chloride) of fine-particle silicon can be favorably influenced by surface-bound chlorine.

Accordingly, the present invention relates to fine-particle silicon containing surface-bound halogen.

According to the invention, at least every 1,000th and preferably at least every 100th surface atom of the fine-particle silicon should be a halogen atom. At most every second surface atom should be a halogen atom. In a particularly preferred embodiment, the ratio of silicon atoms to halogen atoms is between 3 and 20. The particle diameter of the fine-particle silicon according to the invention is determined by the intended application and is generally between 20 and 500 μm. An average particle diameter of 80 to 200 μm is preferred for use in Rochow's synthesis, the particle size distribution being between 40 and 400 μm.

Although the investigations on which the present invention is based were carried out with a view to the use of the fine-particle silicon in Rochow's synthesis, the fine-particle silicon according to the invention may also be used with advantage in other chemical reactions with silicon providing the surface-bound halogen.

Halogens in the context of the invention are fluorine, chlorine, bromine or iodine. Chlorine is the preferred halogen.

The present invention also relates to a process for producing the fine-particle silicon containing surface-bound halogen.

In its most general form, the process according to the invention for the production of fine-particle silicon containing surface-bound chlorine is characterized in that fine-particle silicon is contacted in reactive form with halogen or gaseous or liquid halogen compounds.

The process is described hereinbelow with reference by way of example to chlorine as the preferred halogen.

Particularly suitable chlorine compounds are those consisting of elements which are present in any case in Rochow's synthesis.

Accordingly, suitable chlorine compounds are methyl chloride and chlorosilanes, such as silicon tetrachloride, hydrogen trichlorosilane, methyl trichlorosilane, dimethyl dichlorosilane or trimethyl monochlorosilane. The preferred silane is silicon tetrachloride.

In one embodiment of the process according to the invention, fine-particle silicon is heated in a chlorine-containing atmosphere to a temperature above 250° C. Nitrogen gas containing 2 to 10% by volume chlorine may be used for the chlorine-containing atmosphere. However, this embodiment is less preferred on account of the aggressiveness of chlorine.

In another embodiment of the process according to the invention, coarse-particle silicon is ground in chlorosilane, more particularly silicon tetrachloride. The reactive parts of the silicon are the particular freshly broken surfaces formed. Grinding may be carried out both in suspension with silicon tetrahalide as the suspension medium or at a temperature above the boiling point of silicon tetrachloride of 57.6° C. in an atmosphere of silicon tetrachloride. Grinding is preferably carried out in a closed mill of which the atmosphere is completely replaced by silicon tetrachloride. In the case of other halogens, the temperature of the mill is increased beyond the boiling temperature of the particular silicon tetrahalides ($SiBr_4$; 152.8° C., $SiI_4$: 287.5° C.).

In a third variant of the process according to the invention, untreated silicon which has already been finely ground is initially introduced, subsequently converted into the reactive form by heating to a temperature of at least 900° C. and then exposed to an inert gas atmosphere containing silicon tetrachloride. Nitrogen, for example, may be used for the inert gas atmosphere. The necessary reaction time is determined on the one hand by the temperature of the silicon and the content of silicon tetrachloride in the atmosphere. Reaction times of a few seconds are generally sufficient.

In one preferred embodiment of this third variant of the process, fine-particle silicon is allowed to trickle through a graphite tube heated to a temperature above 1,000° C. and preferably between 1,100° and 1,300° C., a container holding liquid silicon tetrachloride being arranged beneath the graphite tube to collect the fine-particle silicon. On trickling through the graphite tube, in which the atmosphere is of silicon tetrachloride, the fine-particle silicon is highly heated so that its surface reacts with the silicon tetrachloride. As they emerge from the lower end of the graphite tube, the silicon particles very quickly lose their heat through radiation and are quenched as they drop into the liquid silicon tetrachloride so that the reaction is terminated. The fine-particle silicon obtained containing surface-bound chlorine is removed in the form of a suspension at the bottom of the silicon tetrachloride container and is then separated from the suspension liquid.

The silicon tetrachloride in the collecting container is preferably kept at a temperature just below the boiling point so that the atmosphere in the graphite tube can be controlled in this way.

Fine-particle silicon obtained by atomization from the melt is preferably used as the fine-particle silicon in the process according to the invention.

In the fourth and particularly preferred variant of the process according to the invention, a silicon melt is atomized in an atmosphere of silicon tetrachloride. Atomization is preferably carried out by the so-called disk projection method in which a melt strand issuing from a crucible holding the melt at approximately 1,600° C. impinges on a disk rotating at high peripheral speed and is tangentially projected from the disk so that the melt is broken up into fine droplets. The spinning disk is accommodated in a vessel which contains an atmosphere of silicon tetrachloride and of which the conical base contains liquid silicon tetrachloride kept by suitable cooling just below the boiling temperature of the silicon tetrachloride, for example at 40° C. The fine-particle silicon projected from the spinning disk reacts with the silicon tetrachloride, cools down quickly in the silicon tetrachloride atmosphere and is collected in the liquid silicon tetrachloride at the bottom of the vessel from which it can be continuously removed and then separated from adhering silicon tetrachloride.

A liquid level of silicon tetrachloride is preferably maintained at the bottom of the vessel by continuous removal of the silicon tetrachloride vapor formed from the atomization vessel, condensation and cooling of the vapor and return of liquid cooled silicon tetrachloride near the liquid level of the atomization vessel.

In one particularly preferred variant of the disk projection method, silicon tetrachloride is continuously applied as cooling medium to the spinning disk. A corresponding method and a suitable apparatus are described in U.S. Pat. No. 4,347,199.

A particularly suitable method for producing the fine-particle silicon according to the invention on an industrial scale is characterized in that the silicon melt is dispersed by the action of gases flowing at high speed, vaporous silicon tetrachloride being at least partly used as the gas. An apparatus suitable for this process is described in U.S. Pat. No. 4,469,313.

The fine-particle silicon according to the invention hydrolyzes with moisture at its surface with formation of hydrogen halide. Accordingly, it has to be stored in the absence of air.

The process according to the invention affords particular advantages when it is directly combined with the subsequent Rochow synthesis for the production of dimethyl dichlorosilane.

The combined process is characterized in that liquid silicon is dispersed under the effect of gas streams, methyl chloride being used for the gas streams.

A fine-particle silicon suspended in methyl chloride gas and containing surface-bound chlorine is obtained and, after cooling to around 300° C., is directly transported into the Rochow reactor in the form of a fluidized bed reactor.

The invention will be further described with reference to the accompanying drawing, wherein:

FIG. 1 is a schematic view of an apparatus suitable for producing fine-particle silicon and using it in a Rochow synthesis in accordance with the present invention; and FIG. 2 is an enlarged front view of the slot nozzle in FIG. 1.

Referring now more particularly to the drawing, in FIG. 1 there is shown a crucible 1 with heating means 2 for melting silicon. Liquid silicon flows out through the opening 3 in the bottom of the crucible 1. By means of a slot nozzle 4 which consists of a stainless steel tube pressed together at its orifice (see reference 5 in FIG. 2), a jet of gaseous methyl chloride is directed onto the silicon melt stream issuing from the crucible opening 3, so that the silicon melt is broken up into fine droplets.

By lowering the silicon bar 6, the crucible 1 is kept full over a period of several hours.

The flow tube 7 opens into a reactor 9 at the bottom (11) of which methyl chloride heated to 300° C. and nitrogen are introduced through a perforated plate 10 in such a quantity that the silicon powder remains fluidized in the reactor, but is not discharged at the top (12) thereof. At the opening of the perforated plate 10, the reactor 9 has an internal diameter of 4 cm and widens to six times the cross-sectional area at its widest point. It has a length of 110 cm. The temperature of the reactor 9 is kept at 300° C. 160 g silicon are atomized per hour.

At the lower end of the reactor 9, a very fine-particle (<10 μm) catalyst mixture of copper catalyst and ZnO is pneumatically introduced with nitrogen through a feed pipe 8 into the methyl chloride stream carrying the silicon powder so that, on average, 8 g copper catalyst and 0.125 ZnO are used per 100 g silicon.

Product gases, unreacted methyl chloride and nitrogen issue from the head 12 of the reactor. The product gases are separated off by condensation.

EXAMPLE 1

Silicon powder (type A: foreign metal content: 0.26% Fe, 0.14% Al, 0.058% Ca, 0.022% Ti; particle size distribution 71–160 μm) was introduced into a quartz tube (internal diameter 22 mm, length 59 cm) and heated under nitrogen to 900° C.

After a temperature of 900° C. was reached, the nitrogen atmosphere was replaced by an $SiCl_4$ atmosphere (gradual evaporation of 100 ml $SiCl_4$) and heated for another 2 h at 900° C.

The silicon powder was cooled under nitrogen to room temperature.

40 g of this silicon powder, 3.2 g copper catalyst and 0.05 g ZnO were introduced under nitrogen into, and homogenized in, a stirred bed reactor of glass (internal diameter 30 mm) which was equipped with a spiral stirrer. Methyl chloride was passed through the catalyst from below via a glass frit under a pressure of 2 bar. The methyl chloride stream was kept constant and amounted to approximately 1.8 l/h. After heating and initiation of the reaction, a stationary test phase was established at 300° C. and the percentage dimethyl dichlorosilane content relative to the accumulating mixture of monomeric silanes was determined under the conditions thus established.

A dimethyl dichlorosilane content of 91.4% by weight was obtained as the average value of four individual determinations.

EXAMPLE 2 (Comparison Example)

In the reaction of untreated silicon powder (type A: as in Example 1) under the same conditions as in Example 1, a percentage dimethyl dichlorosilane content in the monomeric silane mixture of 90.8% by weight was determined.

EXAMPLE 3

70 g coarse-particle silicon (type B: particle size distribution: <5 mm, foreign metal specification: 0.38% Fe; 0.15% Al; 0.005% Ca; 0.02% Ti) were suspended in 70 ml silicon tetrachloride in a Retsch KM 1 mortar mill and ground for 2 minutes. The suspension was then filtered under nitrogen and the silicon powder was dried for 1 hour in a water jet vacuum.

40 g of the silicon powder ($D_{50}$=82 µm) thus prepared were introduced under nitrogen into the stirred bed reactor described in Example 1 together with copper catalyst and ZnO, homogenized and reacted under the conditions described in Example 1.

The dimethyl dichlorosilane content thus determined was 91.2% by weight.

EXAMPLE 4 (Comparison Example)

Silicon (type B: same specification as in Example 3) was similarly ground in the mortar mill in the absence of silicon tetrachloride (see Example 3).

40 g of the untreated silicon powder were reacted together with 3.2 g copper catalyst and 0.05 g ZnO under the same boundary conditions as in Example 1.

A dimethyl dichlorosilane content of 90% by weight was obtained.

EXAMPLE 5

Silicon (type A, see Example 1) was melted in a laboratory atomizing unit similar in structure to that described in U.S. Pat. No. 4,347,199 and was atomized in an $SiCl_4$ atmosphere by means of a spinning disk to which liquid $SiCl_4$ was centrally applied as coolant.

The test which was not optimized in regard to the atomizing conditions produced an Si powder of widely varying particle size.

A 75 to 150 µm diameter (sieve size) particle fraction was recovered from the silicon powder thus obtained by sieving in a nitrogen atmosphere.

40 g of the silicon powder were reacted with methyl chloride under the conditions of Example 1. 6.8 g/h of a silane mixture containing 91.8% by weight dimethyl dichlorosilane were obtained.

EXAMPLE 6

Silicon (type A, see Example 1) was melted and processed in the apparatus of FIG. 1 under the conditions described hereinabove in connection with the drawing.

After 5 hours of operation, the dimethyl dichlorosilane content in the silane mixture obtained was 93.8% by weight.

EXAMPLE 7 (Comparison Example)

The procedure was as in Example 6, except that, instead of methyl chloride, nitrogen was blown in through the nozzle 4. At 11, the nitrogen introduced in addition to methyl chloride was replaced by methyl chloride, so that the ratio of nitrogen to methyl chloride in the reactor 9 was the same as in Example 6.

The dimethyl dichlorosilane content in the silane mixture obtained was 91.0% by weight.

EXAMPLE 8 (Comparison Example)

The procedure was as in Example 7, except that the crucible 1 was removed and the nozzle 4 is replaced by a feed pipe through which 160 g/h ground silicon were pneumatically introduced with nitrogen after preheating to 300° C. The dimethyl dichlorosilane content in the silane mixture obtained was 90.2% by weight.

It will be understood that the specification and examples are illustrative but not limitative of the present invention and that other embodiments within the spirit and scope of the invention will suggest themselves to those skilled in the art.

We claim:

1. An improved process for the production of organochlorosilanes by the direct reaction of silicon particles, having particle sizes of from 20 to 500 µm, with an organochloride in the presence of a copper catalyst, wherein the improvement comprises binding a halogen to the surface of said silicon particles before said silicon particles are reacted with said organochloride in the presence of said copper catalyst by
    a) making said silicon particles by grinding silicon to a particle size of 20 to 500 µm in the presence of silicon tetrachloride; or
    b) heating said silicon particles to a temperature of at least 900° C. add then exposing said heated particles to an inert gas containing silicon tetrachloride; or
    c) heating said silicon particles in a silicon tetrachloride atmosphere and then quenching said particles in liquid silicon tetrachloride; or
    d) melting silicon and atomizing the resulting melt in an atmosphere of silicon tetrachloride; or
    e) making said silicon particles by melting silicon and dispersing the resulting melt in a stream of gas consisting at least partly of vaporous silicon tetrachloride.

2. The process of claim 1, wherein said silicon particles are made by grinding silicon to a particle size of 20 to 500 µm in the presence of silicon tetrachloride.

3. The process of claim 1, wherein said halogen is chlorine, and is bound to said silicon particles by heating said silicon particles to a temperature of at least 900° C. and then exposing said heated particles to an inert gas containing silicon tetrachloride.

4. The process of claim 1, wherein said silicon particles are made by heating silicon particles in a silicon tetrachloride atmosphere and then quenching said particles in liquid silicon tetrachloride.

5. The process of claim 1, wherein said silicon particles are made by melting silicon and atomizing the resulting melt in an atmosphere of silicon tetrachloride.

6. The process of claim 1, wherein said silicon particles are made by melting silicon and dispersing the resulting melt in a stream of gas consisting at least partly of vaporous silicon tetrachloride.

7. The process of claim 2, wherein said organochlorosilane is methylchlorosilane.

8. The process of claim 3, wherein said organochlorosilane is methylchlorosilane.

9. The process of claim 4, wherein said organochlorosilane is methylchlorosilane.

10. The process of claim 5, wherein said organochlorosilane is methylchlorosilane.

11. The process of claim 6, wherein said organochlorosilane is methylchlorosilane.

* * * * *